US006342629B1

(12) United States Patent
Nakazawa

(10) Patent No.: US 6,342,629 B1
(45) Date of Patent: Jan. 29, 2002

(54) PROCESS FOR PRODUCTION OF OPTICALLY ACTIVE N-PROTECTED-N-METHYL-PHENYLALANINE DERIVATIVE

(75) Inventor: Masakazu Nakazawa, Kawaski (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/495,360

(22) Filed: Feb. 1, 2000

(30) Foreign Application Priority Data

Jul. 14, 1999 (JP) .......................................... 11-200014

(51) Int. Cl.⁷ ........................ C07B 55/00; C07C 229/00
(52) U.S. Cl. ........................ 562/401; 562/402; 562/445
(58) Field of Search ................................. 562/401, 402, 562/445

(56) References Cited

U.S. PATENT DOCUMENTS

| | | | |
|---|---|---|---|
| 3,907,638 A | * | 9/1975 | Uzuki et al. |
| 4,351,763 A | * | 9/1982 | Gesellchen et al. |
| 5,248,813 A | * | 9/1993 | Manimaran et al. |
| 5,543,423 A | | 8/1996 | Zelle et al. |

FOREIGN PATENT DOCUMENTS

| | | |
|---|---|---|
| WO | WO 96/15101 | 5/1996 |
| WO | WO 97/46252 | 12/1997 |

OTHER PUBLICATIONS

Shiraiwa et al. Racemic structures and optical resolution by preferential crystallization of organic ammonium salts of N–formyl–DL–phenylalanine. Bull. Chem. Soc. Jpn, 53, 2331–2334, 1986.*

Katsuura et al. Derwent Abstract of Jp 4100101626A. Production of high purity optically active amino acid or its hydrochloride.*

Okamoto, et al, Memoirs Of The Faculty Of Science "Syntheses of Optically Active N–Methylamino Acids and Their Dicyclohexylamine Salts", Kyushu University, Kukuoka, Japan, Ser. C. vol., 9, No. 1, 1974, pp. 131–137.

A. Prahl, et al., Collection of Czechoslovak Chemical Communications, vol. 62, No. 12, pp. 1940 to 1946, "Influence Of C–Terminal Modifications Of Bradykinin Antagonists On Their Activity", 1997.

Derwent Publications, AN 1977–24641Y, JP 52 008821, Mar. 11, 1977.

* cited by examiner

Primary Examiner—Paul J. Killos
Assistant Examiner—Mahreen Chaudhry
(74) Attorney, Agent, or Firm—Oblon, Spivak, McClelland, Maier & Neustadt, P.C.

(57) ABSTRACT

There is provided a process for industrially and efficiently producing an optically active N-protected-N-methyl-4-halogenophenylalanine at a high purity, which is useful as an intermediate for the production of pharmaceutical agents.

An optically active N-protected-N-methyl-4-halogenophenylalanine (including the free form and/or the salt form thereof) purified to a high purity is produced by way of the deposition and isolation in the form of salt (DCHA salt or the like) from an optically active N-protected-N-methyl-4-halogenophenylalanine containing at least the optical isomer thereof as an impurity. Because the intended compound at a high purity can be recovered and obtained at a high yield, the process of the present invention is very useful as a process for producing the intermediate for the production of pharmaceutical agents.

18 Claims, No Drawings

US 6,342,629 B1

PROCESS FOR PRODUCTION OF OPTICALLY ACTIVE N-PROTECTED-N-METHYL-PHENYLALANINE DERIVATIVE

BACKGROUND OF THE INVENTION

1. Field of the Invention

The present invention relates to a novel process for producing an optically active N-protected-N-methyl-phenylalanine derivative; more specifically, the invention relates to a novel process for producing an optically active N-protected-N-methyl-4-halogenophenylalanine purified chemically and optically to a high purity. The derivative is important as an intermediate for the production of pharmaceutical agents; and in accordance with the invention, the derivative at such a high purity chemically and optically that the derivative can sufficiently be used as the intermediate for the production of pharmaceutical agents can be produced very efficiently and industrially.

2. Description of the Background

Optically active N-protected-N-methyl-4-halogenophenylalanine, for example N-tert-butyloxycarbonyl-N-methyl-L-4-chlorophenylalanine, is known to be useful as an intermediate for the production of pharmaceutical agents (see PCT Japanese Patent Kohyou Publication No. JP-A-10-509151).

So as to use the phenylalanine derivative as an intermediate for the production of pharmaceutical agents, it is required to industrially produce the compound purified chemically and optically to a high purity.

SUMMARY OF THE INVENTION

According to the findings of the present inventors, optically active N-protected-N-methyl-4-halogenophenylalanine can be produced by subjecting optically active N-protected-4-halogenophenylalanine, for example N-tert-butyloxycarbonyl-L-4-chlorophenylalanine to N-methylation step but contains the optical isomer thereof as a part of impurities therein. However, it is difficult to remove the optical isomer as an impurity contained in the derivative thus prepared, even by subjecting the derivative to crystallization step, so the intended optical purity cannot readily be yielded. Thus, it is difficult to produce the derivative at a high purity chemically and optically, and at a high yield by such a method. The repetition of the crystallization step makes the production process laborious and involves the reduction of the yield, which is not preferable industrially. Therefore, it is needed to develop a process for industrially and efficiently producing an optically active N-protected-N-methyl-4-halogenophenylalanine, chemically and optically purified to a high purity.

It is a purpose of the present invention to develop a process for industrially and efficiently producing the optically active form purified to such a high purity that the optically active form can sufficiently be used as an intermediate for the production of pharmaceutical agents.

DETAILED DESCRIPTION OF THE PREFERRED EMBODIMENTS

So as to solve the problem, the present inventors have made investigations with efforts and have found that when a salt is recovered (deposited) by subjecting an optically active N-protected-N-methyl-4-halogenophenylalanine at least containing the optical isomer thereof as an impurity to a step of salt formation and is then isolated, the optical isomer and the like as impurities contained therein are nearly removed from the resulting salt and that an optically active N-protected-N-methyl-4-halogenophenylalanine purified to a high purity can be recovered at a high yield by subjecting the salt thereby recovered to desalting. Thus, the present invention has been achieved.

The isolation of the optical isomer as an impurity is not readily done by the crystallization procedure of the free form, but through the process of salt formation, the impurity can be removed very efficiently. Hence, the intended compound at a highly chemical and a highly optical purity can be recovered at a high yield, taking the subsequent crystallization procedure of the free form into consideration.

In other words, the present invention relates to a process for producing an optically active N-protected-N-methyl-4-halogenophenylalanine at a high purity (including a free form thereof and/or a salt form thereof), comprising the steps of: subjecting an optically active N-protected-N-methyl-4-halogenophenylalanine containing at least the optical isomer thereof as an impurity to a process of salt formation to deposit (precipitate) it and isolating the salt of the optically active form. The production of an optically active form, which may be in the free form or in the salt form such as dicyclohexylamine salt) of the intended compound, at least by way of the separation or isolation step in the form of salt in such manner, is encompassed with the scope of the present invention.

Additionally, the ultimate purpose in accordance with the present invention is the acquisition (recovery) of the optically active form purified to a high purity at a high yield, which is useful as an intermediate for the production of pharmaceutical agents.

Meanwhile, the DCHA salt of an optically active N-protected-N-methyl-phenylalanine with no substituent at 4-position of the phenyl group has already been known (see Memoirs of the Faculty of Science, Kyushu University Ser. C, Vol. 9, No. 1, 1974, 131–138). According to the reference, however, the free form of the N-protected-N-methyl-phenylalanine is in the form of oily matter and has therefore physical properties different from those of the subject compound of the present invention, of which the free form is recovered in a solid state. According to the reference, additionally, the compound is first prepared as DCHA salt and is then isolated in a solid state, but the reference never includes any description suggesting the purification effect as described in the present invention. Further, the problem to be solved by the present invention, namely final efficient acquisition (recovery) of the free form at a high purity, is never present in the reference.

The substance to be purified in accordance with the present invention is an optically active N-protected-N-methyl-4-halogenophenylalanine containing at least the optical isomer thereof as an impurity. A halogen atom, preferably chlorine atom or bromine atom, is present at 4-position of the phenyl group composing the phenylalanine derivative.

The purpose lies in the production of the optically active form as an intermediate for the production of pharmaceutical agents and the optically active form then may satisfactorily be any of the L and D forms. For producing the L form at a high purity as the intended compound, the optical isomer as an impurity corresponds to the D form of the intended compound; for producing the D form, the impurity corresponds to the L form.

Such impurity in the form of isomer contained in the substance to be purified in accordance with the present invention generally contaminates the substance through side reactions in the course of the production for the intended compound. From the respect of purification efficiency, the content of the isomer as an impurity is preferably about 1 to 10% by weight, more preferably about 1 to 5% by weight, and still more preferably about 1 to 3% by weight. By the process of the present invention, a purified product (in the form of salt or in the free form) can be obtained at an optical purity of 99.0% ee or more, optically preferably.

The amino group of the above-mentioned phenylalanine derivative as the intended compound in accordance with the present invention has a protective group; and as the protective group, protective groups for general use for amino group are illustrated, such as tert-butyloxycarbonyl group (Boc), benzyloxycarbonyl group (Z), and 9-fluorenylmethyloxycarbonyl group (Fmoc).

The optically active N-protected-N-methyl-4-halogenophenylalanine of the present invention can be produced by the N-protection and N-methylation of 4-halogenophenylalanine (optically active form).

For carrying out the N-protection and N-methylation of 4-halogenophenylalanine (optically active form), the protective method for the amino group of amino acid and general methods known as N-methylation method can be adopted. For the N-methylation, a method comprising the reaction of sodium hydride with methyl iodide is general. For the production in practice, satisfactorily, the N-protection (with Boc and the like) is first effected, followed by the N-methylation. It is needless to say that an optically active form at a high optical purity is preferably used as the 4-halogenophenylalanine (optically active form), but even in that case, optical isomer impurities are generated by side reactions and contaminate the resulting product through the steps of the N-protection and N-methylation.

For producing an optically active 4-halogenophenylalanine, herein, an already known method is utilized, whereby the optically active 4-halogenophenylalanine can readily be produced. For example, a method comprising introducing an intended halogen atom at 4-position of the phenyl group in an optically active phenylalanine [see J. Med. Chem., 17(5), 556 (1974)] can be listed.

Additionally, a synthesis method by way of aminomalonic acid derivative [see Tetrahedron: Asymmetry, 9, 3274 (1998)] is also used. More specifically, 2-acylamino-2-(4-halogenobenzyl)-malonate diester, preferably 2-acetylamino-2-(4-halogenobenzyl)-malonate diester (diethyl ester and the like) is hydrolyzed with alkali and the like, to prepare N-acyl (acetyl and the like)-DL-halogenophenylalanine, which is then allowed to react with acylase, to obtain (recover) the intended (desired) optically active form at a high purity. Herein, the raw material of 2-acylamino-2-(4-halogenobenzyl)malonate diester can readily be produced by allowing 2-acylaminomalonate diester and 4-halogenobenzyl halide to react together.

In accordance with the present invention, the intended optically active form as the principal component is preferentially deposited in the form of salt and then isolated during the process of salt formation of the substance to be purified, whereby impurities such as optical isomer can be removed into solvent. The base for composing the salt includes amines such as dicyclohexylamine (DCHA) and cyclohexylamine. The DCHA salt is particularly preferable because the DCHA salt is excellent in terms of purification effect.

For the recovery in the form of salt, first, an amine such as DCHA or the like is added to a solvent dissolving therein an optically active N-protected-N-methyl-4-halogenophenylalanine and impurities such as the optical isomer thereof, to precipitate (deposit) the optically active N-protected-N-methyl-4-halogenophenylalanine in the form of salt, which is then isolated, satisfactorily. As the solvent, ethyl acetate, isopropyl acetate, acetone, ethanol, isopropanol and a mixture solvent thereof are listed. Because the crystallinity of the resulting amine salt is excellent, ethyl acetate is particularly preferable. The formation of the salt is effected at a temperature of about 10 to 50° C. in the case that ethyl acetate for example is used as the solvent. Generally, impurities can be removed to a level such that the resulting purified product can sufficiently be used as an intermediate for the production of pharmaceutical agents, by carrying out once such process of salt formation and isolation. In accordance with the present invention, accordingly, the intended compound at a high purity can be obtained at a high yield. Such process of salt formation and isolation can satisfactorily be repeated, but in that case, the yield is reduced. Thus, generally, the repetition is not needed.

For purifying the free form itself by crystallization procedure, not by way of salt form, the purification efficiency is significantly reduced; when it is intended to raise the purity, the yield is significantly reduced.

So as to recover the free form from the thus prepared salt of an optically active N-protected-N-methyl-4-halogenophenylalanine, a generally known method can be used for the conversion to free carboxyl group. Using aqueous solutions prepared by dissolving an acid, for example sulfuric acid and aqueous potassium hydrogen sulfate solution, an extraction procedure is effected for the desalting.

For the recovery of the intended optically active N-protected-N-methyl-4-halogenophenylalanine in the form of salt, generally, a product at a high purity can be recovered, in which impurities have been removed sufficiently, by effecting the process of salt formation and isolation as described above. For the recovery thereof in the free form, the resulting salt thus prepared (in which impurities have been removed sufficiently at the process of salt formation and isolation) is desalted, from which the solvent dissolving the free form therein is then distilled off, whereby an optically active N-protected-N-methyl-4-halogenophenylalanine in a solid form at a high purity can readily be recovered and obtained. However, the crystallization procedure for the recovery thereof in the crystalline form is rather simple and conventional for industrial production, from the standpoint of the recovery of the intended compound, and furthermore, an additional purification effect can be expected as well, preferably.

For the practice of the crystallization, a known crystallization procedure can be utilized. A solution dissolving therein the intended compound is subjected to crystallization by an appropriate combination of general crystallization means such as cooling in atmosphere, concentration, cooling, addition of seed crystal, standing, and agitation (stirring). Specifically, a poor solvent such as heptane, hexane, toluene, xylene, methyl-tert-butyl ether, etc. is added to the free form at a state dissolved in a solvent, for example ethyl acetate, isopropyl acetate, acetone, ethanol, isopropanol, etc., whereby the free form can readily be crystallized and isolated, to obtain the intended compound.

As apparently shown in the descriptions insofar and the descriptions of examples below, an optically active N-protected-N-methyl-4-halogenophenylalanine (including the free form and/or the salt form thereof) purified to a high purity can be produced at a high yield according to the process in the present invention.

EXAMPLES

The invention will now be described in more detail in the following examples and comparative examples. The value in % used in the examples is expressed by % by weight, unless otherwise stated.

Reference Example 1
Production of 2-acetylamino-2-(4-chlorobenzyl)-malonate Diethyl Ester

[Chemical formula 1]

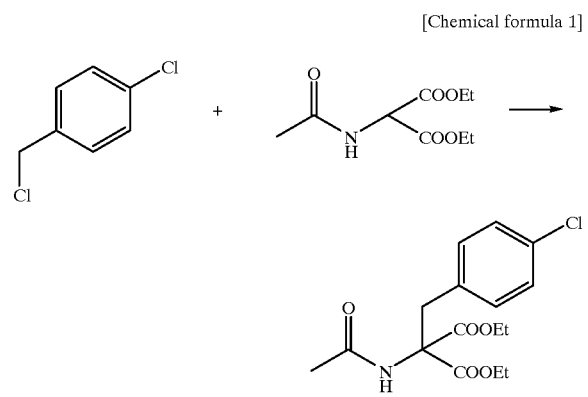

102.3 g of 20% sodium ethoxide-ethanol solution and 65.1 g of 2-acetylaminomalonate diethyl ester were added to 400 ml of ethanol and were then dissolved therein under agitation. 48.3 g of 4-chlorobenzyl chloride was added to the resulting solution, for reflux under heating for 4 hours. After the termination of the reaction, 350 ml of ethanol was distilled off by concentration under reduced pressure, to isolate the deposited crystal. The crystal was washed with 50 ml of ethanol, to recover 87.4 g of the intended compound (wet) (pure content of 76.6 g, yield of 75%).

EXAMPLE 1
Production of N-acetyl-DT-4-chlorophenylalanine

[Chemical formula 2]

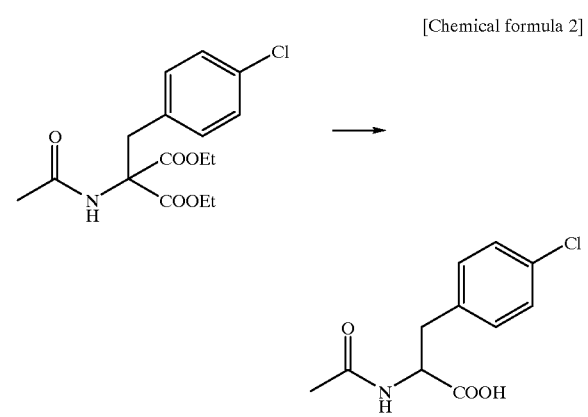

87.4 g (pure content of 76.6 g) of the 2-acetylamino-2-(4-chlorobenzyl)-malonate diethyl ester (wet) recovered above was dissolved in 225 ml of ethanol. 225 ml of water and 26 g of aqueous 48% potassium hydroxide solution were added to the resulting solution, for reflux under heating for 2 hours. Further, 26 g of an aqueous 48% potassium hydroxide solution was added to the resulting solution, for reflux under heating for 2 hours. After the termination of the reaction, 400 ml of water and 50 ml of conc. hydrochloric acid were added to the reaction mixture, which was thereby adjusted to pH 1. The crystal then precipitated was isolated and washed with 50 ml of water, to obtain (recover) the intended compound (wet) of 103.7 g (pure content of 54.4 g, yield of 100%).

EXAMPLE 2
Production of L-4-chlorophenylalanine

[Chemical formula 3]

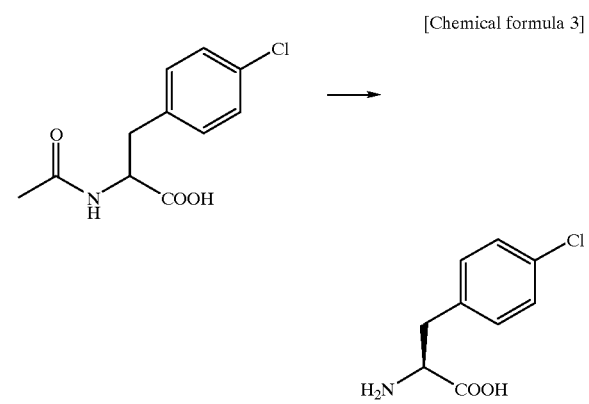

282.8 g (pure content of 158.6 g) of the N-acetyl-DL-4-chlorophenylalanine (wet) recovered above was suspended in 750 ml of water, followed by addition of 70 ml of an aqueous 27% sodium hydroxide solution to adjust the suspension to pH 7, so that the N-acetyl-DL-4-chlorophenylalanine was dissolved therein. Insoluble matters were removed by filtration, and 0.2 g of cobalt chloride and 2.0 g of acylase were added to the resulting filtrate, which was agitated overnight at 37° C., under addition of an aqueous 6 mol /1 liter sodium hydroxide solution to adjust the mixture to pH 7. The resulting mixture was cooled to 15° C. or lower, followed by addition of 6 mol /1 liter hydrochloric acid for adjustment to pH 6, and the deposited crystal was isolated, to obtain 90.4 g of the intended compound (wet) (pure content of 54.5 g, yield of 41.4%).

EXAMPLE 3
Production of N-tert-butyloxycarbonyl-L-4-chlorophenyl alanine

[Chemical formula 4]

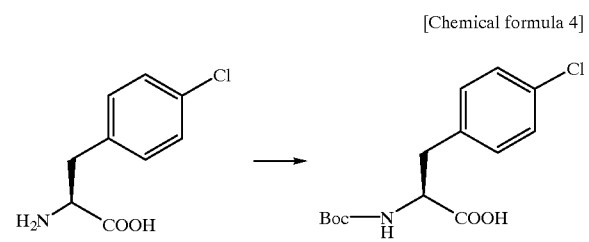

77.2 g (pure content of 46.5 g) of the L-4-chlorophenylalanine (wet) obtained above was dissolved in 200 ml of water and 29.2 ml of an aqueous 27% sodium hydroxide solution, followed by addition of a solution of 55.9 g of di-tert-butyl dicarbonate in 160 ml of methanol and subsequent agitation at 30° C. for 4 hours. 200 ml of methanol and water were distilled off by concentration under reduced pressure, and to the resulting solution were added 450 ml of ethyl acetate and 40 ml of 6 mol/1 liter hydrochloric acid to adjust the solution to pH 3, for extraction. The ethyl acetate layer was washed with 200 ml of saturated aqueous sodium chloride solution. The ethyl acetate layer was concentrated to 200 ml solution, followed by addition of 800 ml of n-heptane for crystallization. The precipitated crystal was isolated and washed with 70 ml of n-heptane. The crystal was then dried overnight at 40° C. under reduced pressure, to obtain 57.0 g of the intended compound (yield of 81.6%, purity of 99.0% or more, optical purity of 99.0% ee or more).

EXAMPLE 4
Production of N-tert-butyloxycarbonyl-N-methyl-L-4-chlorophenylalanine

[Chemical formula 5]

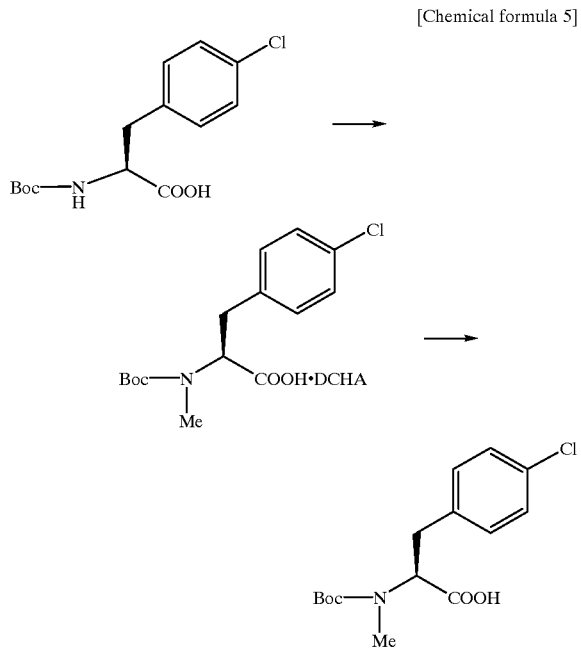

5.0 g of 60% sodium hydride was added to 75 ml of tetrahydrofuran (THF) under cooling on ice. 50 ml of a solution of 15 g of N-tert-butyloxycarbonyl-L-4-chlorophenylalanine in THF was added to the resulting mixture at the same temperature, followed by further addition of 8.0 ml of methyl iodide. The resulting mixture was agitated at 40° C. for 24 hours, followed by the addition of 50 ml of water and 1.8 ml of 6 mol /1 liter hydrochloric acid, and from which THF was distilled off by concentration under reduced pressure. 150 ml of ethyl acetate and 6 mol /1 liter hydrochloric acid were added to the resulting aqueous solution, to adjust the solution to pH 2.5, for extraction. The ethyl acetate layer was washed sequentially with 50 ml of an aqueous 5% sodium thiosulfate (sodium hyposulfite) solution, 50 ml of water and 50 ml of aqueous saturated sodium chloride solution in this order. N-tert-butyloxycarbonyl-N-methyl-4-chlorophenylalanine in the ethyl acetate solution was at 95.4% ee. The ethyl acetate solution was heated to 50° C., to which was then added 10 ml of dicyclohexylamine for agitation. The deposited dicyclohexylamine salt was isolated by filtration, and washed with 20 ml of ethyl acetate. 120 ml of ethyl acetate and 120 ml of an aqueous 5% potassium hydrogen sulfate solution were added to the resulting crystal (wet), and the mixture was then agitated. The agitated solution was partitioned into layers; and the resulting ethyl acetate layer was sequentially washed twice with 50 ml of an aqueous 5% potassium hydrogen sulfate solution, once with 50 ml of water and with 50 ml of aqueous saturated sodium chloride solution in this order. The ethyl acetate layer was concentrated under reduced pressure, and 50 ml of n-heptane was added to the resulting residue, which was again concentrated under reduced pressure. To the resulting residue were added 100 ml of n-heptane and 5 ml of ethyl acetate, for crystallization. The deposited crystal was isolated, washed with 20 ml of n-heptane, and dried at 40° C. under reduced pressure overnight, to obtain the intended compound of 11.51 g (yield of 73.4%, purity of 99.7%). The optical purity analyzed by optically active HPLC (high-performance liquid chromatography) exceeded 99.0% ee in the optical purity.

EXAMPLE 5

In the same manner as in Example 4, the reaction was repeated under conditions shown in Table 1 for the same treatment. The results of the aforementioned reactions are shown in Table 1. Herein, the optical purity was measured by using a column with a larger number of theoretical plates.

TABLE 1

| Examples (Comparative Examples) | CH$_3$I (eq) | NaH (eq) | Temperature (° C.) | Optical purity (% ee) of reaction/ extracted solution | Optical purity of DCHA salt (% ee) | Chemical purity (area %) | Optical purity (% ee) | Yield (%) |
|---|---|---|---|---|---|---|---|---|
| 4 | 2.5 | 2.5 | 40 | 95.4 | >99.0 | 99.7 | >99.0 | 73.4 |
| 5 | 2.2 | 2.2 | 40 | 93.2 | >99.0 | 99.8 | >99.5 | 70.8 |
| Comparative Example 1 | 2.5 | 2.5 | 40 | 93.0 | — | 93.4 | 95.3 | 83.2 |
| Comparative Example 2 | 2.2 | 2.2 | 40 | 93.2 | — | 99.0 | 94.8 | 81.6 |
| Comparative Example 3 | 3.0 | 2.5 | 40 | — | — | 99.0 | >99.0 | 54.8 |
| Comparative Example 4 | 2.5 | 2.5 | 50 | — | — | 92.3 | 93.2 | 66.6 |

Comparative Examples 1 to 4

Production of N-tert-butyloxycarbonyl-N-methyl-L-4-chlorophenylalanine

[Chemical formula 6]

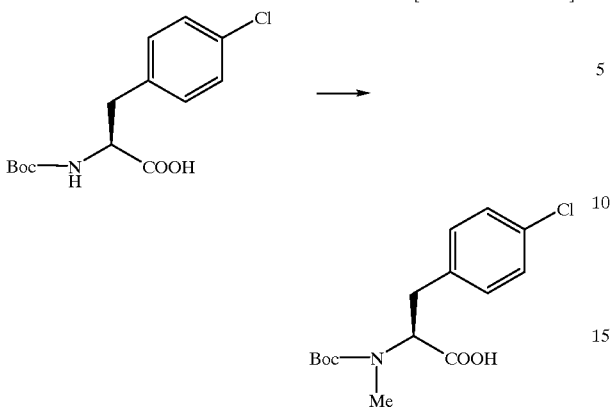

In the same manner as in Example 4, N-methylation was conducted, to prepare a solution of N-tert-butyloxycarbonyl-N-methyl-4-chlorophenylalanine in ethyl acetate (93.4% ee).

With no practice of the step of the deposition of dicyclohexylamine salt, thereafter, the ethyl acetate layer was concentrated, to which was then added n-heptane, for crystallization. Through isolation and drying under reduced pressure, the intended compound was recovered (yield of 83.2%, purity of 93.4%, optical purity of 95.3% ee).

In the same manner as in Comparative Example 1, the reaction was repeated under conditions shown in Table 1, and the same treatment as above was also carried out. The results of the aforementioned reactions are shown in Table 1.

Based on the results in Table 1, it is understandable that it is difficult to isolate an optical isomer contained as an impurity in the intended compound recovered in crystal, not by way of salt form. Thus, the optical purity can never be raised and improved when the yield of the intended optically active form is to be retained.

In accordance with the present invention, it is understandable that the free form recovered by way of the step of isolation of the intended optically active form in the salt form is extremely excellent in terms of optical purity, in particular, and that the process of the present invention is industrially advantageous with no laborious repetition of another crystallization step.

On purification of an optically active N-protected-N-methyl-4-halogenophenylalanine containing at least the optical isomer thereof as an impurity, by subjecting the optically active N-protected-N-methyl-4-halogenophenylalanine to a salt formation process, and isolating the precipitated salt (DCHA salt or the like), the impurities contained therein such as the optical isomer can be efficiently separated and removed, and by desalting the resulting salt, the free form purified to a high purity can be obtained at a high yield. Thus, the process in the present invention is very useful as an industrial process for producing the intermediate for the production of pharmaceutical agents.

What is claimed is:

1. A process for producing an optically active N-protected-N-methyl-4-halogenophenylalanine, which is in a free form, comprising the steps of:
    a) forming a cyclohexylamine or dicyclohexylamine salt of the optically active N-protected-N-methyl-4-halogenophenylalanine containing at least an optical isomer thereof as an impurity, said optical isomer thereof as an impurity being contained in an amount of 10% by weight or less therein; and
    b) isolating the formed salt of the optically active form, and generating the free form thereof.

2. The process of claim 1, wherein the protective group for said N-position in the phenylalanine compound is tert-butyloxycarbonyl group (Boc), benzyloxycarbonyl group (Z) or 9-fluorenylmethyloxycarbonyl group (Fmoc).

3. The process of claim 2, wherein the protective group for said N-position in the phenylalanine compound is tert-butyloxycarbonyl group (Boc).

4. The process of claim 1, wherein said free form of step b) is the L-form, and the impurity is the D-form.

5. The process of claim 1, wherein said free form of step b) is the D-form, and the impurity is the L-form.

6. The process of claim 1, wherein said free form of the optically active compound has an optical purity of at least 99.0% ee.

7. The process of claim 1, wherein said optically active N-protected-N-methyl-4-halogenophenylalanine containing at least the optical isomer thereof as an impurity is produced by effecting N-protection and N-methylation of an optically active 4-halogenophenylalanine.

8. The process of claim 7, wherein the optically active 4-halogenophenylalanine is produced by reacting an acylase with N-acyl-DL-halogenophenylalanine produced by hydrolysis of 2-acylamino-2-(4-halogenobenzyl)-malonate diester.

9. The process of claim 1, wherein the optically active N-protected-N-methyl-4-halogenophenylalanine is N-tert-butyloxycarbonyl-N-methyl-L-4-chlorophenylalanine.

10. The process of claim 1, wherein the salt is the dicyclohexylamine salt.

11. The process of claim 1, wherein the optical isomer impurity is present in said optically active N-protected-N-methyl-4-halogenophenylalanine in step a) in an amount of about 1 to 5% by wt.

12. The process of claim 11, wherein said optical isomer impurity is present in an amount of about 1 to 3% by wt.

13. The process of claim 1, wherein the formed salt of the optically active form is isolated by precipitation.

14. The process of claim 13, wherein said salt is formed in ethyl acetate as a solvent.

15. The process of claim 14, wherein said salt is formed at a temperature in a range of about 10 to 50° C.

16. An optically active N-protected-N-methyl-4-halogenophenylalanine in a free form having an optical purity of 99.0% ee or more.

17. The compound of claim 16, which is in an L-form.

18. The compound of claim 16, which is in a D-form.

* * * * *

UNITED STATES PATENT AND TRADEMARK OFFICE
CERTIFICATE OF CORRECTION

PATENT NO. : 6,342,629 B1
DATED : January 29, 2002
INVENTOR(S) : Masakazu Nakazawa It is certified that error appears in the above-identified patent and that said Letters Patent is hereby corrected as shown below:

Column 1,
Lines 35 and 51, delete the spaces after "cally" and after "active".

Column 5,
Line 12, "Diethyl" should read "diethyl".
Line 42, "N-acetyl-DT-4-chlorophenylalanine" should read
-- N-acetyl-DL-4-chlorophenylalanine --.

Signed and Sealed this

Fourth Day of June, 2002

Attest:

JAMES E. ROGAN
Attesting Officer      Director of the United States Patent and Trademark Office